(12) United States Patent
Liphardt

(10) Patent No.: US 8,600,703 B1
(45) Date of Patent: Dec. 3, 2013

(54) METHOD OF EVALUATING DATA QUALITY

(75) Inventor: Martin M. Liphardt, Lincoln, NE (US)

(73) Assignee: J.A. Woollam Co., Inc, Lincoln, NE (US)

( * ) Notice: Subject to any disclaimer, the term of this patent is extended or adjusted under 35 U.S.C. 154(b) by 378 days.

(21) Appl. No.: 12/653,299

(22) Filed: Dec. 11, 2009

Related U.S. Application Data

(60) Provisional application No. 61/201,473, filed on Dec. 12, 2008.

(51) Int. Cl.
  *G01J 4/04* (2006.01)
  *G01B 11/06* (2006.01)

(52) U.S. Cl.
  USPC ............... 702/172; 250/559.09; 356/369

(58) Field of Classification Search
  USPC ............. 702/90, 172; 356/369; 250/559.09
  See application file for complete search history.

(56) References Cited

U.S. PATENT DOCUMENTS

| | | | | |
|---|---|---|---|---|
| 5,486,701 A | * | 1/1996 | Norton et al. | 250/372 |
| 5,748,317 A | * | 5/1998 | Maris et al. | 356/502 |
| 5,798,837 A | * | 8/1998 | Aspnes et al. | 356/369 |
| 6,034,777 A | * | 3/2000 | Johs et al. | 356/369 |
| 6,128,080 A | * | 10/2000 | Janik et al. | 356/491 |
| 6,633,831 B2 | * | 10/2003 | Nikoonahad et al. | 702/155 |
| 7,043,325 B1 | * | 5/2006 | Adams, III | 700/109 |
| 7,151,605 B1 | | 12/2006 | Herzinger et al. | 356/369 |
| 7,307,724 B1 | * | 12/2007 | Liphardt et al. | 356/369 |
| 2002/0015146 A1 | * | 2/2002 | Meeks et al. | 356/73 |
| 2004/0033617 A1 | * | 2/2004 | Sonbul | 436/171 |
| 2004/0207845 A1 | * | 10/2004 | Opsal et al. | 356/369 |

OTHER PUBLICATIONS

Gutierrez-Osuna, "Signal Processing Methods for Drift Compensation", May 2003, 2nd NOSE II Workshop, pp. 1-60 http://research.cse.tamu.edu/prism/lectures/talks/nose03.pdf.*

Method and Apparatus for Measuring Thickness of Thin Films or Substrate, EP 1 577 636 by Dianippon Screen, Published Sep. 21, 2005.

* cited by examiner

*Primary Examiner* — Drew A Dunn
*Assistant Examiner* — Regis Betsch
(74) *Attorney, Agent, or Firm* — James D. Welch

(57) ABSTRACT

Methodology for determining uncertainty in a data set which characterizes a sample involving elimination of the influence of sample alteration drift caused by data set acquisition, and/or elimination of the influence of system drift during data acquisition.

12 Claims, 9 Drawing Sheets

METHOD OF EVALUATING DATA QUALITY

CROSS-REFERENCE TO EXISTING APPLICATIONS

This Application claims Benefit of Provisional 61/201,473 Filed Dec. 12, 2008.

TECHNICAL FIELD

The present invention relates to data quality, and more particularly to methodology for determining uncertainty in a data set which characterizes a sample involving elimination of the influence of sample alteration drift caused by data set acquisition, and also elimination of the influence of system drift during data acquisition.

BACKGROUND

It is known in the areas of Ellipsometry, Polarimetry and Reflectometry or the like, to acquire a data set, (e.g. intensity, Ellipsometric PSI, Ellipsometric DELTA over Time), which characterizes a sample, by causing a beam of electromagnetic radiation to interact with the sample, and determining changes in the beam caused by said interaction.

It is also known that the act of observing a sample can cause change to occur thereto. For instance, especially over a prolonged time needed to make a plurality of measurements, energy delivered to a sample by a beam of electromagnetic radiation impinging thereupon can catalyze reaction of the sample surface with said atmospheric components to the end that deposition of said atmospheric components occurs onto said sample. This can lead to a measurable change, (i.e. sample drift), of, for instance, measured film thickness on said sample surface over time.

It is also known that data acquisition systems such as ellipsometers and reflectometers can change, (i.e. systemic drift), during application thereof in monitoring a sample, leading to acquisition of data which falsely represents sample composition.

Known patents which address handling data sets are:
U.S. Pat. No. 7,151,605 to Herzinger et al. describes a method of replacing data points in a data set determined to be bad, while maintaining the remainder of the data set; and
U.S. Pat. No. 7,307,724 to Liphardt et al. describes a method reducing the effect of noise in a data set.

Another known patent, while not directly related to the handling of data sets is:
Patent to Johs et al., U.S. Pat. No. 6,034,777 which describes a method for compensating for the effects of the presence of polarization state affecting input/output, elements in an ellipsometer system.

Another reference identified is an EPO Application titled "Method and Apparatus for Measuring Thickness of Thin Films on Substrate", No. EP 1 577 636 B1 by Dianippon Screen Mfg., published 21 Sep. 2005.

Need exists for methodology that allows compensating for sample and/or systemic drift during data acquisition.

DISCLOSURE OF THE INVENTION

The present invention provides methodology for compensating a data set obtained over time, for drift in sample composition and/or drift in the operation of the data acquisition system that produces the data set.

In general, as noted, Data vs. Time can include slope based on two sources, (Sample change and Measurement System change), which for two Sample points can be expressed:

DATA SLOPE$_1$=SYSTEM DRIFT+SAMPLE DRIFT$_1$; and

DATA SLOPE$_2$=SYSTEM DRIFT+SAMPLE DRIFT$_2$.

Further, a ratio of Sample Point Exposure Times $T_1$ and $T_2$ is:

$R_{12}=T_1/T_2$; and $R_{21}=T_2/T_1$.

It is noted that the Data Slopes 1 and 2 are observed to be, and are generally considered to be first order straight line fits to plotted acquired data, such as typically determined by least square error procedures.

For emphasis, it is stated directly that the change in a Sample based on exposure to an electromagnetic beam is presumed to be proportional to exposure time. For instance, if Sample Point 2 is exposed for a longer time than Sample Point 1, Point 2 will be affected to a greater extent, which is proportional to the ratio of exposure times. Other than linear dependencies are possible, and the quality of the linear correction dependents on the accuracy of this assumption. It is noted that for non-linear dependencies other equations, (e.g. polynomial), can be derived.

Continuing, in all following cases, the present invention methodology begins with:
a) providing a system comprising:
  a source of a beam of electromagnetic radiation;
  a sample supporting stage;
  means for controlling where a beam of electromagnetic radiation from said source thereof impinges on a sample placed on said stage; and
  a detector of electromagnetic radiation which exits said sample.

Case 1

In the case of the method of compensating a sample characterizing data set for sample drift, the methodology further comprises:
b) causing said beam of electromagnetic radiation to impinge on a position on said sample so that it interacts therewith and enters said detector, so that said detector provides as output, a plurality of data points over time;
said plurality of data points acquired in step b serving to identify sample drift if a plot thereof presents with an overall slope.
Said method then further comprises:
c) if the plurality of data points acquired from the position in step b present with an overall slope, compensating said plurality of data points acquired in step b for the identified sample drift;
to the end that a sample characterizing data set which is compensated for sample drift is achieved.

Case 2

In the case of compensating a sample characterizing data set for system drift during data acquisition, the methodology further comprises:
b) causing a beam of electromagnetic radiation to impinge on a first position on said sample so that it interacts therewith and enters said detector, so that said detector provides as output, a first single data point in a brief period of time;
c) causing said beam of electromagnetic radiation to impinge on a second position on said sample so that it interacts therewith and enters said detector, so that said detector provides as output, a plurality of data points over time;

d) causing said beam of electromagnetic radiation to again impinge on said first position on said sample so that it interacts therewith and enters said detector, so that said detector provides as output, a second single data point in a brief period of time;

said first and second data points acquired from said first position on said sample in steps b and d serving to identify data acquisition system drift if they are different and a plot thereof presents with an overall slope; and said plurality of data points acquired in step c serving to identify sample drift if a plot thereof presents with an overall slope.

Said method then further comprises:

e) if the first and second data points acquired from said first position on said sample in steps b and d are different, compensating said plurality of data points acquired from the second position in step c for the identified system drift during data acquisition;

to the end that a sample characterizing data set which is compensated for data acquisition system drift during data acquisition is achieved.

Case 3

In the case of the method of compensating a sample characterizing data set for sample and system drift during data acquisition, the methodology further comprises:

b) causing a beam of electromagnetic radiation to impinge on a first position on said sample so that it interacts therewith and enters said detector, so that said detector provides as output, a first single data point in a brief period of time;

c) causing said beam of electromagnetic radiation to impinge on a second position on said sample so that it interacts therewith and enters said detector, so that said detector provides as output, a plurality of data points over time;

d) causing a beam of electromagnetic radiation to again impinge on said first position on said sample so that it interacts therewith and enters said detector, so that said detector provides as output, a second single data point in a brief period of time;

said first and second data points acquired from said first position on said sample in steps b and d serving to identify data acquisition system drift if they are different and a plot thereof presents with an overall slope; and said plurality of data points acquired in step c serving to identify sample drift if a plot thereof presents with an overall slope.

Said method then further comprises:

e) if the first and second data points acquired from said first position on said sample in steps b and d are different, compensating said plurality of data points acquired from the second position in step c for the identify data acquisition system drift; and f) if the plurality of step e compensated second position step c acquired data points still present with an overall slope, compensating said plurality of data points acquired in step c for the identified sample drift;

to the end that a sample characterizing data set which is compensated for sample and system drift during data acquisition is achieved.

In the foregoing Cases 1, 2 and 3 it is to be considered that the Time (T1) of application of an electromagnetic beam to a first location on a sample is far less than the time (T2) of application of an electromagnetic beam to a second location on a sample, (e.g., a T2/T1>=about 10). A Case 4, wherein the times (T1) and (T2) are far less different from one another, (e.g. T2/T1 is <=about 5, and optionally can even be equal to one another, or T1/T2 can be <=about 5), will be treated in a Continuation Application.

In any of the cases the system provided in step a can further comprise a polarization state generator and a polarization state detector and the system to form an ellipsometer or polarimeter.

In the foregoing, as it is important, where data is acquired over a prolonged period of time at a point on a sample, energy deposited at that point can cause change of the sample, such as, for instance, by deposition of atmospheric components. Data acquired will reflect this influence as a "sample drift". While it is always difficult, where data acquisition times become more and more equal at two sample points, (e.g. one time is less than 5 times the other), it becomes progressively more and more difficult to separately identify sample and system drift slope components in an observed plot. However, data acquired at one of the points on the sample can be acquired during comparatively very short time periods. A basic assumption/premise of the present invention is that where acquisition time is comparatively short, data will not be significantly influenced by sample drift, but rather essentially only by system drift. Hence, where one sample point is investigated very quickly and another over a much longer, (e.g. 10 times longer), time, it becomes possible to easily separately determine system and sample drift components.

It is also noted that when correcting a data set for drift an overall slope can be used at each data point, or a slope obtained in the region of a data point can be used for that point.

It is noted that in the above that Cases 1-3 are each a special case of a general scenario, based on values of $R_{12}$.

For Cases 1 and 2, $R_{12}$ is arbitrary, and:

For Case 1 Observed Data Change=Sample Drift; and

For Case 2 Observed Data Change=System Drift.

For Case 3 $R_{12}$ or $R_{21}$ can be small.

Further, for Cases 1-3, the data slope change could be modeled by a non-linear equation, (e.g. a polynomial or other mathematical equation).

The disclosed present invention methodology can also include performing at least one selection from the group consisting of:

storing at least some data provided by said detector in machine readable media;

analyzing at least some of the data provided by said detector and storing at least some of the results of said analysis in machine readable media;

displaying at least some data provided by said detector by electronic and/or non-electronic means;

analyzing at least some of the data provided by said detector and displaying at least some of the results of said analysis by electronic and/or non-electronic means;

causing at least some data provided by said detector to produce a signal which is applied to provide a concrete and tangible result; and analyzing at least some of the data provided by said detector and causing at least some thereof to produce a signal which is applied to provide a concrete and tangible result.

The present invention will be better understood by reference to the Detailed Description Section of this Specification, with reference to the Drawings.

DETAILED DESCRIPTION

Figure 1:
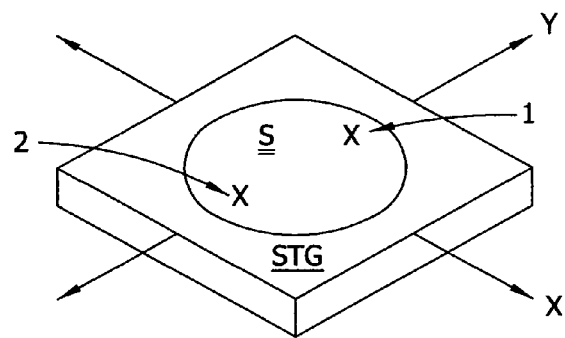
FIG. 1 shows a Sample (S) on a Stage (STG) which, it is indicated, a Means for Directing a Beam (B) of Electromagnetic Radiation from said Source (LS) thereof to impinge on a Sample (S) placed on said Stage (STG), and for controlling where upon said Sample (S) said Beam (B) impinges can be moved to position the Sample (S).

Turning now to the Drawings, FIG. 1 shows a Sample (S) on a Stage (STG) which, it is indicated, can be moved in demonstrative "X" and "Y" directions to position the Sample (S) so that points (1) and (2) can be accessed. Other systems for accomplishing this, such as R-Theta stages, are to be considered equivalent.

Figure 2:
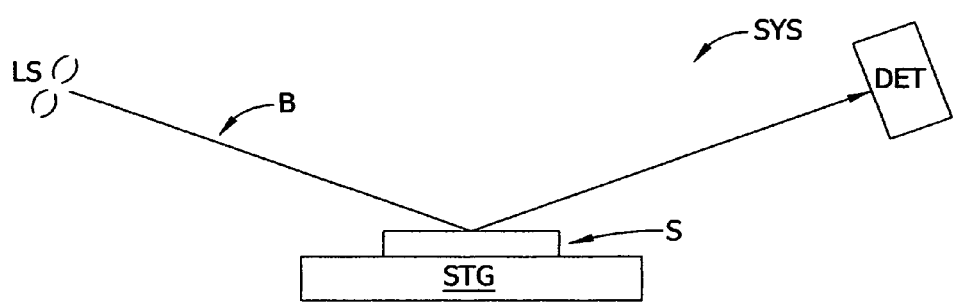
FIG. 2 shows a Data Acquisition System (SYS) for use in obtaining a Data Set.

FIG. 2 shows a Data Acquisition System (SYS) for use in obtaining a Data Set. The Data Acquisition System (SYS) comprises:
 a Source (LS) of a beam (B) of electromagnetic radiation;
 a Sample (S) Supporting Stage (STG);
 a detector of electromagnetic radiation which exits said sample;

In view of the above, it is further noted that FIG. 1 indicates a Means for Controlling where a Beam (B) of Electromagnetic Radiation from said Source (LS) thereof impinges on a Sample (S) placed on said Stage (STG), (i.e. for instance, Point "1" or Point "2"), via indication of "X" and "Y" movements. This could also be accomplished by an R-THETA stage or the like.

Figure 3:
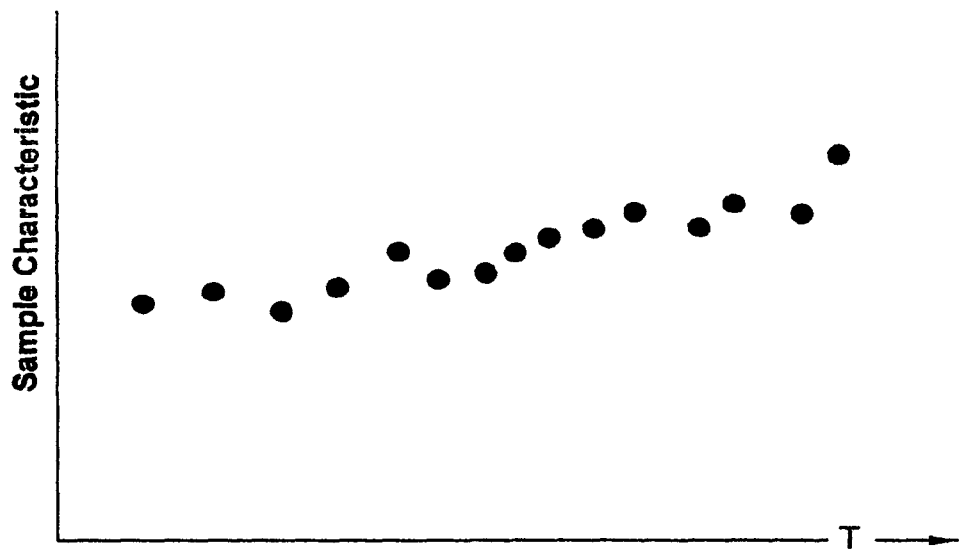
FIGS. 3 and 4 show plots of data indicating sample drift, and data corrected therefore, respectively, where system drift is negligible.
Figure 4:
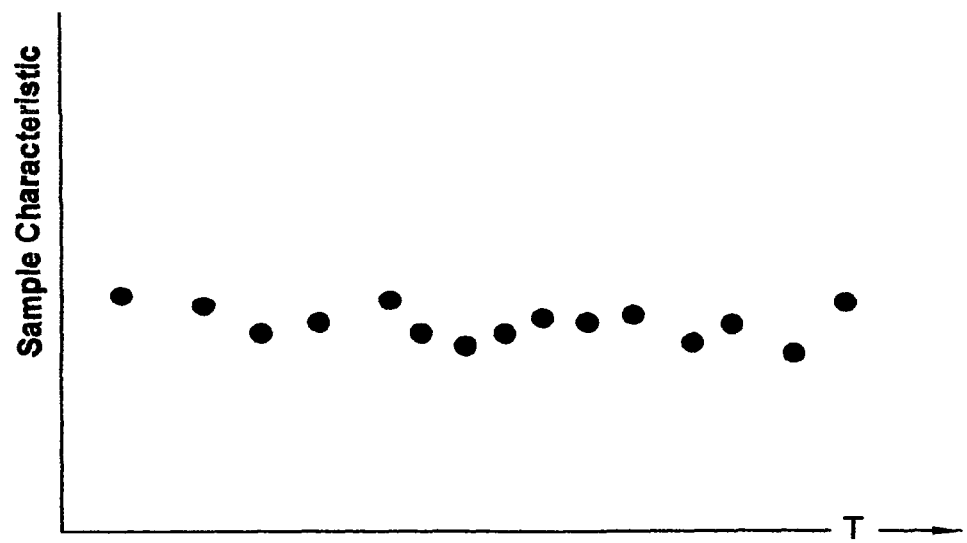
Figure 5:
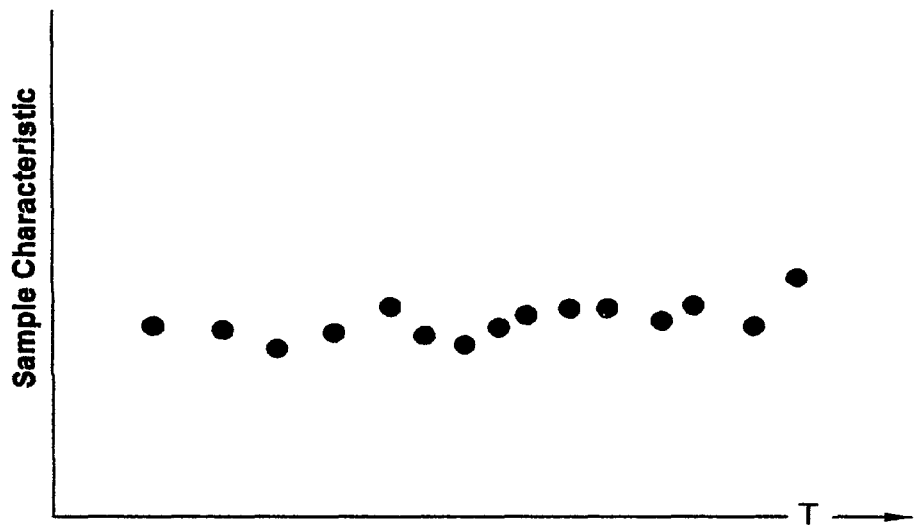
FIG. 5 shows data corrected for sample drift, but wherein system drift is not zero.

FIGS. 3 and 4 show very general introductory plots indicating sample drift, and data corrected for said sample drift, respectively, where system drift is negligible. The plots are best interpreted as demonstrative of data obtained from a single position on a sample over time. FIG. 5 shows, very generally, data which is corrected for sample drift, can still have imposed thereupon a slope resulting from system drift which occurs during data acquisition and is not zero. FIGS. 8-14 which are described below, better disclose what FIGS. 2-5 generally disclose, in the specific context of the present invention methodology.

Figure 6:
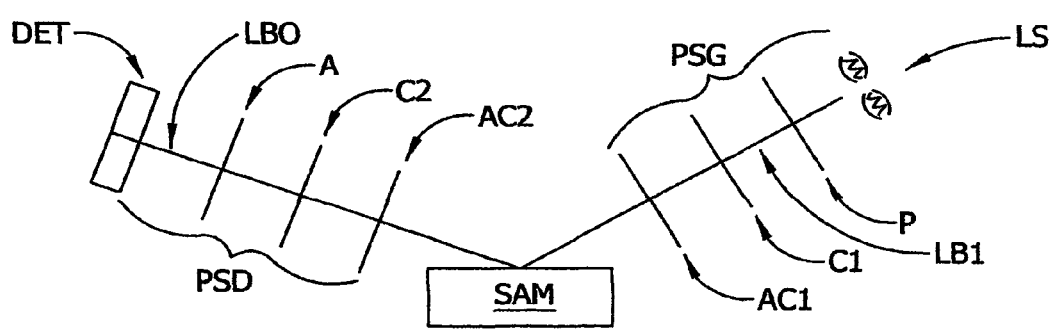
FIG. 6 shows the elements of an Ellipsometer or Polarimeter.

Continuing, as application of the present invention is particularly well suited for use in Ellipsometers and Polarimeters, FIG. 6 is included to show the basic elements of an Ellipsometer or Polarimeter. Note the presence of a Polarization State Generator (PSG) which serves to set a state of polarization in a Beam (B) of Electromagnetic Radiation provided by the Source (LS) thereof. Accompanying is a Polarization State Analyzer (PSA) for determining a change in polarization state caused by interaction with he Sample (SAM). When polarization state is not controlled by application of a (PSG), the system is a Reflectometer or Spectrophotometer. Also note the presence of Arms (SAI) and (SAO) which support the (LS) (PSG) and the (PSA) (DET) respectively. Also note the presence of a Guide (PRIG) for enabling movement of the Beam Directing Means (PRI) into and out of a Beam (B') before it enters the Data Detector (DET). This is a demonstrative, and not limiting, system for effecting the desired result.

Figure 7:
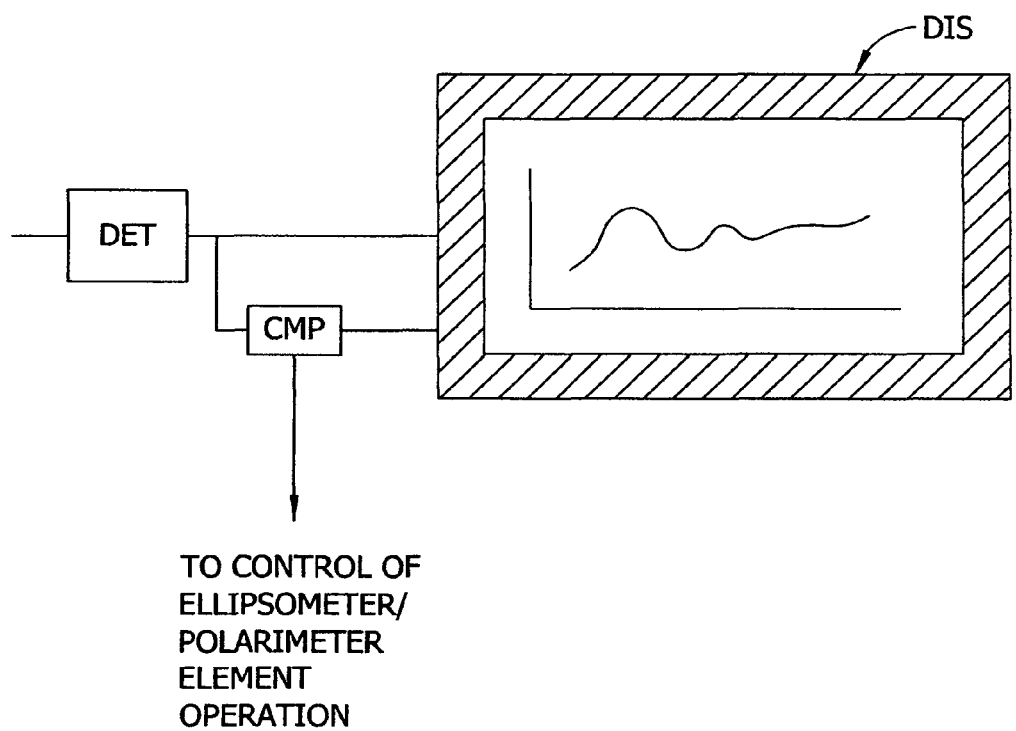
FIG. 7 is included to show that a present invention system can be controlled by a computer.

FIG. 7 is included to show that operation of a present invention system can be controlled by a Computer (CMP). Further, data provided by the Data Detector (DET), or analyzed results thereof, can be presented in a Display (DIS).

Figure 8:
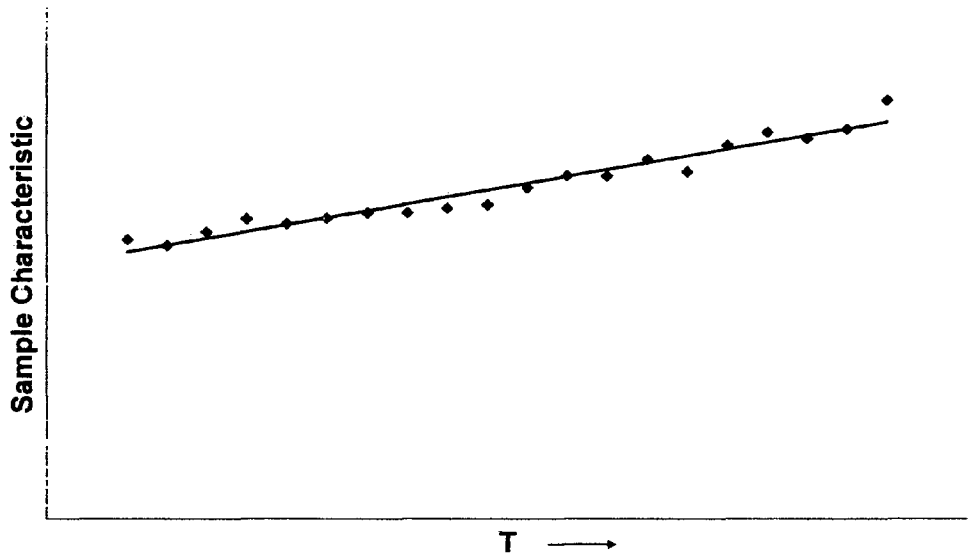
FIGS. 8 and 9 demonstrate a method of removing a first order slope, (the solid line in FIG. 8), to remove the effects of sample drift and arrive at the results shown in FIG. 9.
Figure 9:
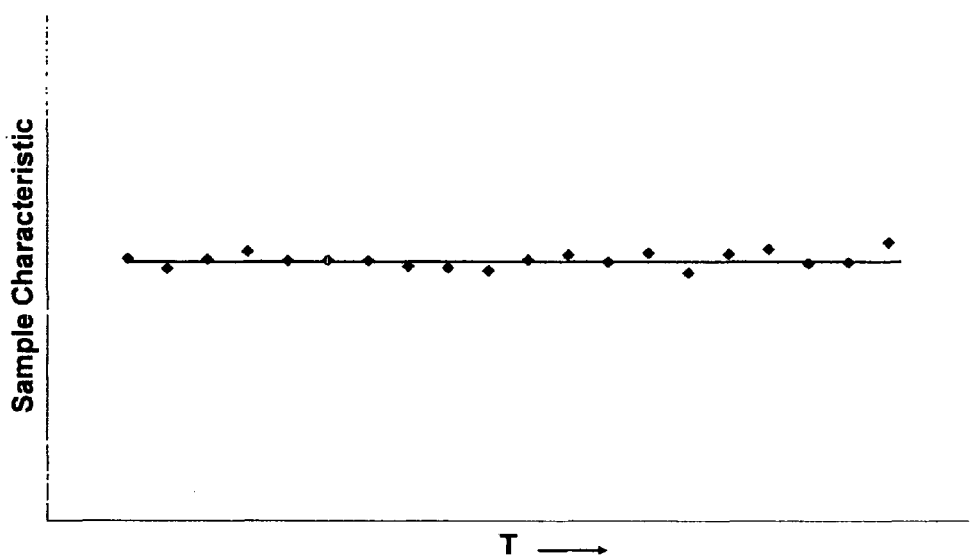

As indicated above, FIGS. 8 and 9 better demonstrate a method of removing a first order slope, (the solid line in FIG. 8), to remove the effects of sample drift and arrive at the results shown in FIG. 9. Said FIGS. 8 and 9 demonstrate the results of practicing the methodology disclosed in the Disclosure of the Invention Section of this Specification which recite:
 b) causing a beam of electromagnetic radiation to impinge on a position on said sample so that it interacts therewith and enters said detector, so that said detector provides as output, a plurality of data points over time;
 said plurality of data points acquired in step b serving to identify sample drift if a plot thereof presents with an overall slope;
 said method further comprising:
 c) if the plurality of data points acquired from the position in step b present with an overall slope, compensating said plurality of data points acquired in step b for the identified sample drift;
to the end that a sample characterizing data set which is compensated for sample drift is achieved.

Figure 10:
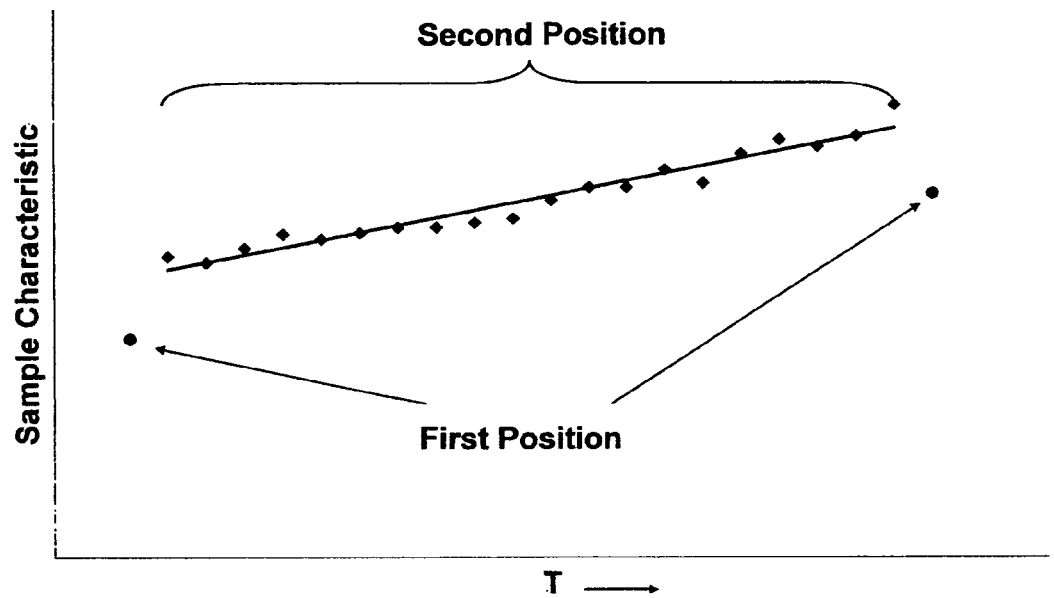
FIGS. 10 and 11 demonstrate a method of removing a first order slope, (the solid line in FIG. 10), to remove the effects of system drift and arrive at the results shown in FIG. 11.
Figure 11:
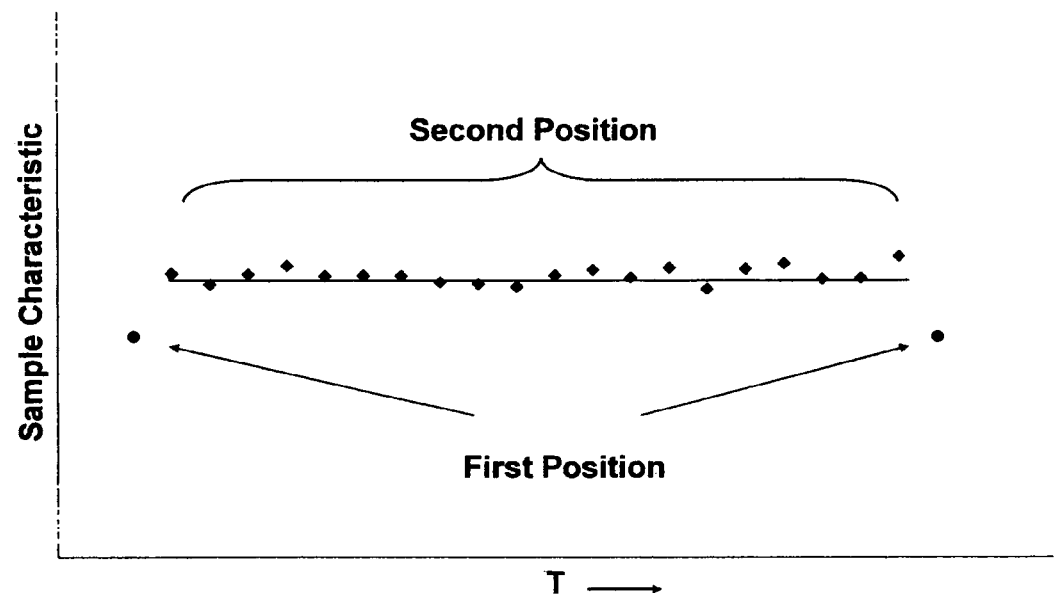

FIGS. 10 and 11 better demonstrate a method of removing a first order slope, (the solid line in FIG. 10), to remove the effects of system drift and arrive at the results shown in FIG. 11. Said FIGS. 10 and 11 demonstrate the results of practicing the methodology disclosed in the Disclosure of the Invention Section of this Specification which recite:
 b) causing a beam of electromagnetic radiation to impinge on a first position on said sample so that it interacts therewith and enters said detector, so that said detector provides as output, a first single data point in a brief period of time;
 c) causing said beam of electromagnetic radiation to impinge on a second position on said sample so that it interacts therewith and enters said detector, so that said detector provides as output, a plurality of data points over time;
 d) causing said beam of electromagnetic radiation to again impinge on said first position on said sample so that it interacts therewith and enters said detector, so that said detector provides as output, a second single data point in a brief period of time;
 said first and second data points acquired from said first position on said sample in steps b and d serving to identify system drift during data acquisition if they are different and a plot thereof presents with an overall slope; and said plurality of data points acquired in step c serving to identify sample drift if a plot thereof presents with an overall slope;
said method further comprising:
e) if the first and second data points acquired from said first position on said sample in steps b and d are different, compensating said plurality of data points acquired from the second position in step c for the identify system drift during data acquisition;
to the end that a sample characterizing data set which is compensated for system drift during data acquisition is achieved.

Figure 12:
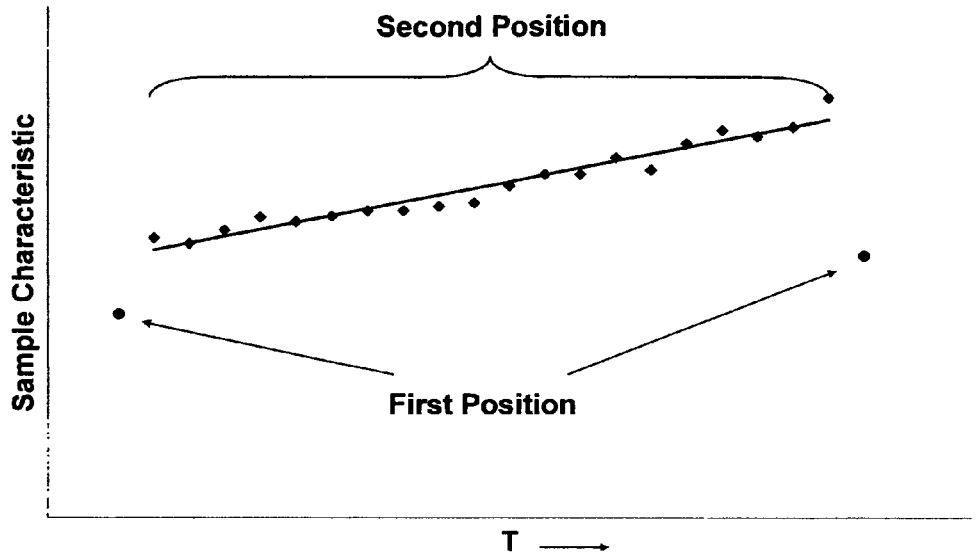
FIGS. 12, 13 and 14 demonstrate a method of removing first order slopes, (the solid lines in FIGS. 12 and 13), to remove the effects of sample drift and system drift, and arrive at the results shown in FIG. 14.
Figure 13:
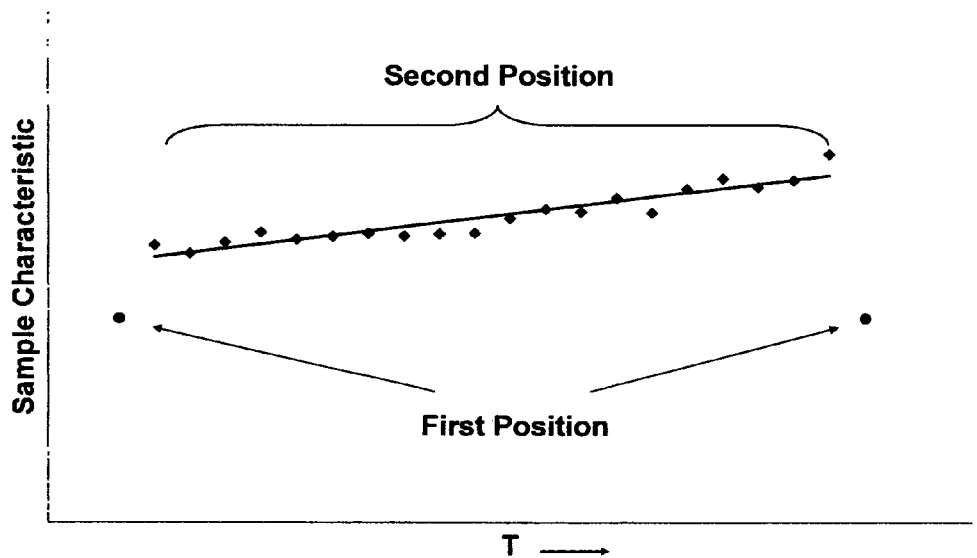
Figure 14:
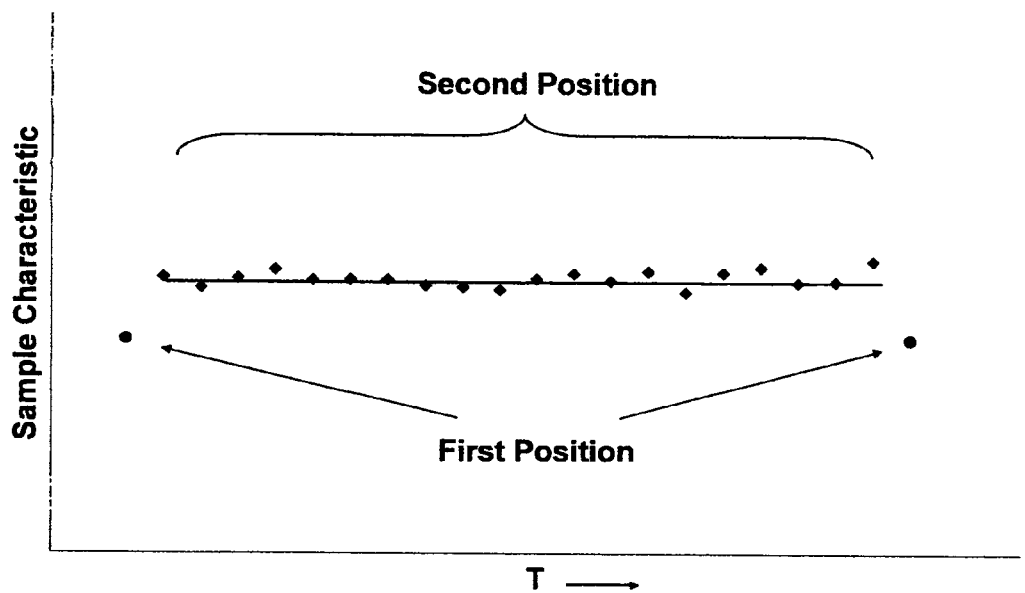

FIGS. 12, 13 and 14 better demonstrate a method of removing first order slopes, (the solid lines in FIGS. 12 and 13), to remove the effects of sample drift and system drift, and arrive at the results shown in FIG. 14. Said FIGS. 12, 13 and 14 demonstrate the results of practicing the methodology disclosed in the Disclosure of the Invention Section of this Specification which recite:
b) causing a beam of electromagnetic radiation to impinge on a first position on said sample so that it interacts therewith and enters said detector, so that said detector provides as output, a first single data point in a brief period of time;
c) causing said beam of electromagnetic radiation to impinge on a second position on said sample so that it interacts therewith and enters said detector, so that said detector provides as output, a plurality of data points over time;
d) causing said beam of electromagnetic radiation to again impinge on said first position on said sample so that it interacts therewith and enters said detector, so that said detector provides as output, a second single data point in a brief period of time;
said first and second data points acquired from said first position on said sample in steps b and d serving to identify system drift during data acquisition if they are different and a plot thereof presents with an overall slope; and
said plurality of data points acquired in step c serving to identify sample drift if a plot thereof presents with an overall slope;
said method further comprising:
e) if the first and second data points acquired from said first position on said sample in steps b and d are different, compensating said plurality of data points acquired from the second position in step c for the identify data acquisition system drift; and
f) if the plurality of step e compensated second position step c acquired data points still present with an overall slope, compensating said plurality of data points acquired in step c for the identified sample drift;
to the end that a sample characterizing data set which is compensated for sample and system drift during data acquisition is achieved.

Figure 15:
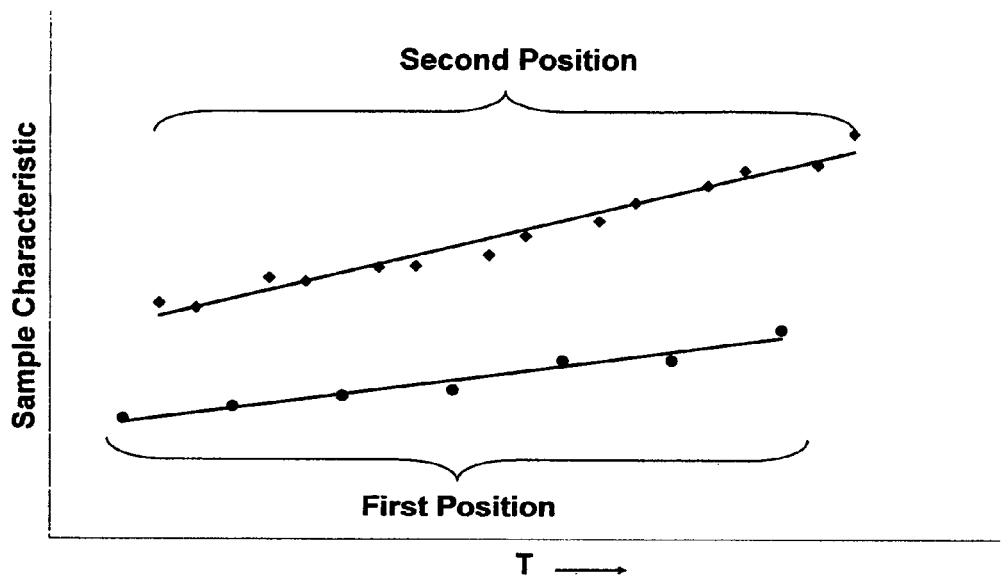
FIGS. 15 and 16 demonstrate a method of removing first order slope, (the solid lines in FIG. 15), to identify the effects of system drift and sample drift where two points on a sample are investigated using similar data acquisition times, and arrive at the results shown in FIG. 16.
Figure 16:
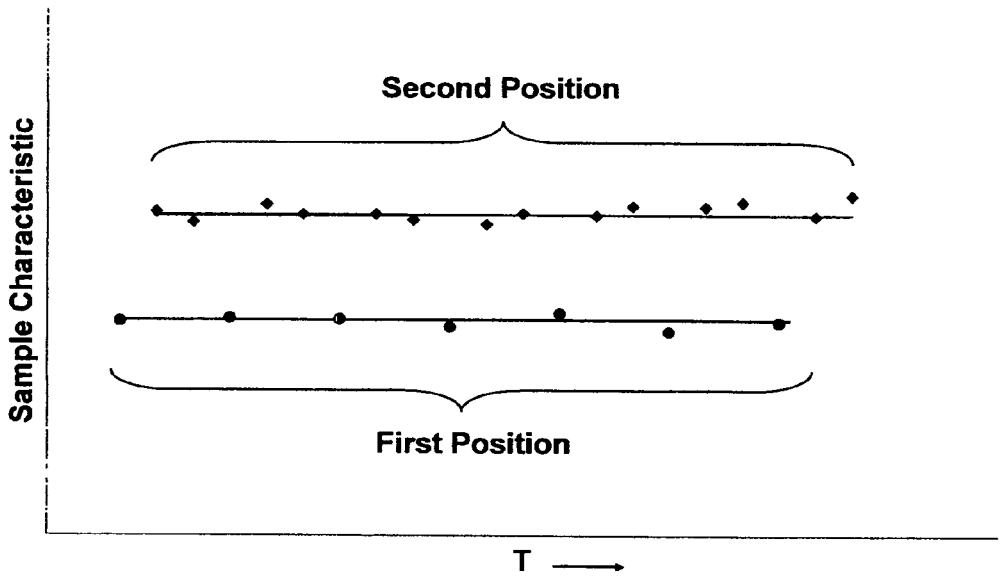

In addition, FIGS. 15 and 16 demonstrate a method of identifying a first order slope, (the solid lines in FIG. 15 which is shown for the case of $R_{12}$ being equal to about 0.5), to identify the effects of system drift and sample drift where two points on a sample are investigated using similar data acquisition times, and arrive at the results shown in FIG. 16. Said FIGS. 15 and 16 demonstrate the results of practicing the methodology of the present invention when times (T1) and (T2) approach being equal, which is a case that will be treated in a Continuation Application.

It is noted that "Sample Characteristics" in FIGS. 8-16 can be any relevant measurable sample characterizing quantity, such as Intensity, Ellipsometric PSI or Ellipsometric DELTA or the like, as well as quantities derived therefrom, (e.g. sample thin film thickness). Also, points (1) and (2) in FIG. 1 correspond to data presented as (First Position) and (Second Position), in FIGS. 8-16.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the claims.

I claim:

1. A method of compensating a sample characterizing data set for system drift during data acquisition, from a sample, comprising, in the recited order, the steps of:
   a) providing a system comprising:
      a source of a single required beam of electromagnetic radiation;
      a sample supporting stage;
      means for controlling where said single required beam of electromagnetic radiation from said source impinges on a sample placed on said stage; and
      a detector of electromagnetic radiation which exits said sample;
   b) causing the single required beam of electromagnetic radiation to impinge on a first position on a sample placed on said sample supporting stage, so that it interacts therewith and enters said detector, so that said detector provides as output, a first single data point in a brief period of time;
   c) causing said single required beam of electromagnetic radiation to impinge on a second, different from said first position on said sample on said sample supporting stage, so that it interacts therewith and enters said detector, so that said detector provides as output, a plurality of data points over time; and
   producing a plot of said plurality of data points as a function of time;
   d) causing said single required beam of electromagnetic radiation to again impinge on said first position on said sample on said sample supporting stage, so that it interacts therewith and enters said detector, so that said detector provides as output, a second single data point in a brief period of time; and
   producing a plot of said first and second data points acquired from said first position on said sample in steps b and d as a function of time;
   e) determining from said first and second data points acquired from said first position on said sample in steps b and d data acquisition system drift if said plot thereof presents with an overall non-zero slope; and
   f) determining from said plurality of data points acquired in step c sample drift caused by said single required beam of electromagnetic radiation-sample interaction, when said plot thereof presents with an overall non-zero slope as a function of time;
   said method further comprising:
   g) if the first and second data points acquired from said first position on said sample in steps b and d are different, then compensating said plurality of data points acquired from the second position in step c for the identified system drift during data acquisition;
to the end that a sample characterizing data set which is compensated for system drift during data acquisition is achieved.

2. A method as in claim 1, in which the system provided in step a further comprises a polarization state generator and a polarization state detector and the system is an ellipsometer or polarimeter.

3. A method as in claim 1 which further comprises at least one selection from the group consisting of:
storing at least some data provided by said detector in machine readable media;
analyzing at least some of the data provided by said detector and storing at least some of the results of said analysis in machine readable media;
displaying at least some data provided by said detector by electronic and/or non-electronic means;
analyzing at least some of the data provided by said detector and displaying at least some of the results of said analysis by electronic and/or non-electronic means;
causing at least some data provided by said detector to produce a signal which is applied to provide a concrete and tangible result; and
analyzing at least some of the data provided by said detector and causing at least some thereof to produce a signal which is applied to provide a concrete and tangible result.

4. A method as in claim 1 wherein the single required beam of electromagnetic radiation source of a beam of electromagnetic radiation is the only electromagnetic radiation intentionally applied to said sample during the obtaining of said data.

5. A method as in claim 1, wherein the system provided in step a, is an ellipsometer or polarimeter.

6. A method of compensating a sample characterizing data set for sample drift resulting during interaction between a monitoring beam of electromagnetic radiation and said sample, and for system drift during data acquisition from a sample, comprising, in the recited order, the steps of:
a) providing a system comprising:
a source of a single required beam of electromagnetic radiation;
a sample supporting stage;
means for controlling where said single required beam of electromagnetic radiation from said source impinges on a sample placed on said stage; and
a detector of electromagnetic radiation which exits said sample;
b) causing the single required beam of electromagnetic radiation to impinge on a first position on a sample placed on said sample supporting stage, so that it interacts therewith and enters said detector, so that said detector provides as output, a first single data point in a brief period of time;
c) causing said single required beam of electromagnetic radiation to impinge on a second, different from the first, position on said sample on said sample supporting stage, so that it interacts therewith and enters said detector, so that said detector provides as output, a plurality of data points over time; and
producing a plot of said plurality of data points as a function of time;
d) causing said single required beam of electromagnetic radiation to again impinge on said first position on said sample on said sample supporting stage, so that it interacts therewith and enters said detector, so that said detector provides as output, a second single data point in a brief period of time; and
producing a plot of said first and second data points acquired from said first position on said sample in steps b and d as a function of time;
e) determining from said first and second data points acquired from said first position on said sample in steps b and d data acquisition system drift when they are different and said plot thereof presents with an overall non-zero slope; and
f) determining from said plurality of data points acquired in step c sample drift, if the plot thereof presents with an overall non-zero slope as a function of time;
said method further comprising:
g) if the first and second data points acquired from said first position on said sample in steps b and d are different, then compensating said plurality of data points acquired from the second position in step c for the identified data acquisition system drift; and
h) if the plurality of step e compensated second position step c acquired data points still present with an overall non-zero slope, then compensating said plurality of data points acquired in step c for the identified sample drift;
to the end that a sample characterizing data set which is compensated for sample and system drift during data acquisition is achieved.

7. A method as in claim 6, in which the system provided in step a further comprises a polarization state generator and a polarization state detector and the system is an ellipsometer or polarimeter.

8. A method as in claim 6 which further comprises at least one selection from the group consisting of:
storing at least some data provided by said detector in machine readable media;
analyzing at least some of the data provided by said detector and storing at least some of the results of said analysis in machine readable media;
displaying at least some data provided by said detector by electronic and/or non-electronic means;
analyzing at least some of the data provided by said detector and displaying at least some of the results of said analysis by electronic and/or non-electronic means;
causing at least some data provided by said detector to produce a signal which is applied to provide a concrete and tangible result; and
analyzing at least some of the data provided by said detector and causing at least some thereof to produce a signal which is applied to provide a concrete and tangible result.

9. A method as in claim 6 wherein the single required beam of electromagnetic radiation source of a beam of electromagnetic radiation is the only electromagnetic radiation intentionally applied to said sample during the obtaining of said data.
said method further comprising:
f) said ellipsometer system computer system recognizing if the first and second data points acquired from said first position on said sample in steps a and c are different, and if they are then said ellipsometer system computer system compensating said plurality of data points acquired from the second position in step b for the identified data acquisition system drift; and
g) said ellipsometer system computer system recognizing if the plurality of step d compensated second position step b acquired data points still vary over time, and if they do then said ellipsometer system computer system compensating said plurality of data points acquired in step b for the identified sample drift;
to the end that a sample characterizing data set which is compensated for sample and system drift during data acquisition is achieved and the results thereof produced by said ellipsometer system computer system.

10. A method as in claim 6, wherein the system provided in step a, is an ellipsometer or polarimeter.

11. A method of compensating a sample characterizing data set for system drift during data acquisition by an ellipsometer system, from a sample:
said ellipsometer system comprising:
- a source of a single required beam of electromagnetic radiation;
- a sample supporting stage;
- means for controlling where said single required beam of electromagnetic radiation from said source impinges on a sample placed on said stage;
- a detector of electromagnetic radiation which exits said sample; and
- a computer system;

said method comprising, in the recited order:
- a) said ellipsometer system causing the single required beam of electromagnetic radiation to impinge on a first position on said sample on said sample supporting stage, so that it interacts therewith and enters said detector, so that said detector provides as output, a first single data point in a brief period of time;
- b) said ellipsometer system causing said single required beam of electromagnetic radiation to impinge on a second, different from said first, position on said sample on said sample supporting stage, so that it interacts therewith and enters said detector, so that said detector provides as output, a plurality of data points over time;
- c) said ellipsometer system causing said single required beam of electromagnetic radiation to again impinge on said first position on said sample on said sample supporting stage, so that it interacts therewith and enters said detector, so that said detector provides as output, a second single data point in a brief period of time;
- d) said ellipsometer system computer system determining from said first and second data points acquired from said first position on said sample in steps a and c data acquisition system drift if they are different; and
- e) said ellipsometer system computer system determining from said plurality of data points acquired in step b sample drift when they vary over time;

said method further comprising:
- f) said ellipsometer system computer system recognizing if the first and second data points acquired from said first position on said sample in steps a and c are different, and if they are then compensating said plurality of data points acquired from the second position in step c for the identified system drift during data acquisition;

to the end that a sample characterizing data set which is compensated for system drift during data acquisition is achieved and the results thereof produced by said ellipsometer system computer system.

12. A method of compensating a sample characterizing data for sample drift during data acquisition by an ellipsometer system, said drift resulting during interaction between a monitoring beam of electromagnetic radiation and said sample, and for system drift during data acquisition from a sample;

wherein said ellipsometer system comprises:
- a source of a single required beam of electromagnetic radiation;
- a sample supporting stage;
- means for controlling where said single required beam of electromagnetic radiation from said source impinges on a sample placed on said stage;
- a detector of electromagnetic radiation which exits said sample; and
- a computer system;
- a) said ellipsometer system causing the single required beam of electromagnetic radiation to impinge on a first position on said sample on said sample supporting stage so that it interacts therewith and enters said detector, so that said detector provides as output, a first single data point in a brief period of time;
- b) said ellipsometer system causing said single required beam of electromagnetic radiation to impinge on a second, different from said first, position on said sample on said sample supporting stage so that it interacts therewith and enters said detector, so that said detector provides as output, a plurality of data points over time;
- c) said ellipsometer system causing said single required beam of electromagnetic radiation to again impinge on said first position on said sample on said sample supporting stage so that it interacts therewith and enters said detector, so that said detector provides as output, a second single data point in a brief period of time;
- d) said ellipsometer system computer system determining from said first and second data points acquired from said first position on said sample in steps a and c non-zero slope data acquisition system drift when they are different and; and
- e) said ellipsometer system computer system determining from said plurality of data points acquired in step b non-zero slope sample drift if they vary over time;

said method further comprising:
- f) said ellipsometer system computer system recognizing if the first and second data points acquired from said first position on said sample in steps a and c are different, and if they are then said ellipsometer system computer system compensating said plurality of data points acquired from the second position in step b for the identified data acquisition system drift; and
- g) said ellipsometer system computer system recognizing if the plurality of step d compensated second position step b acquired data points still vary over time, and if they do then said ellipsometer system computer system compensating said plurality of data points acquired in step b for the identified sample drift;

to the end that a sample characterizing data set which is compensated for sample and system drift during data acquisition is achieved and the results thereof produced by said ellipsometer system computer system.

* * * * *